United States Patent [19]

Smith

[11] Patent Number: 5,900,495
[45] Date of Patent: May 4, 1999

[54] TREATMENTS TO REDUCE ALDOL CONDENSATION POLYMERIZATION REACTIONS DURING THE PRODUCTION OF PROPYLENE OXIDE

[75] Inventor: Gail L. Smith, Spring, Tex.

[73] Assignee: Baker Hughes Incorporated, Houston, Tex.

[21] Appl. No.: 09/042,603

[22] Filed: Mar. 16, 1998

Related U.S. Application Data

[60] Provisional application No. 60/039,192, Mar. 17, 1997.
[51] Int. Cl.⁶ .......................... C07D 303/04; C07C 47/06
[52] U.S. Cl. ........................... 549/512; 549/513; 568/449
[58] Field of Search ................................. 549/512, 513; 568/449

[56] References Cited

U.S. PATENT DOCUMENTS 4,696,983   9/1987   Cohen .

FOREIGN PATENT DOCUMENTS 19510703   5/1996   Germany .

*Primary Examiner*—Johann Richter
*Assistant Examiner*—Taofiq A. Solola
*Attorney, Agent, or Firm*—Madan & Morris, PLLC

[57] ABSTRACT

The present invention provides a method for inhibiting fouling during caustic washing of a propylene oxide product stream comprising treating a solution comprising a propylene oxide product stream and a caustic wash under conditions and with an amount of an amine effective to inhibit said fouling.

25 Claims, No Drawings

TREATMENTS TO REDUCE ALDOL CONDENSATION POLYMERIZATION REACTIONS DURING THE PRODUCTION OF PROPYLENE OXIDE

This application claims the benefit of Provisional Application Ser. No. 60/039,192 filed on Mar. 17, 1997.

FIELD OF THE INVENTION

The present invention relates to the use of certain amines effective to reduce fouling during caustic washing of a propylene oxide product stream.

BACKGROUND OF THE INVENTION

During the production of propylene oxide, the product stream undergoes a caustic wash treatment to remove methyl formate prior to product purification. The propylene oxide product stream that is treated by the caustic wash contains propylene oxide and a large quantity of aldehydes (roughly about 2.5 wt %, primarily acetaldehyde).

Under highly alkaline conditions, lower molecular weight aldehydes, such as acetaldehyde (ethanal), readily undergo base catalyzed aldol condensation at ambient or higher temperatures. The result of such aldol condensation and related reactions is the formation of oligomers and polymers which precipitate out of the wash solution as viscous oils, polymeric gums, and solids. These precipitates can foul the processing equipment and result in the reduction of processing throughput and costly equipment maintenance or repair.

Effective and economical methods are needed for retarding aldol condensation and related reactions during caustic washing of a propylene oxide product stream in order to increase unit run length, reduce maintenance costs, reduce hazardous waste disposal costs, increase production, and reduce personnel exposure.

SUMMARY OF THE INVENTION

The present invention provides a method for inhibiting fouling during caustic washing of a propylene oxide product stream comprising treating a mixture comprising a propylene oxide product stream and a caustic wash under conditions and with an amount of an amine effective to inhibit said fouling.

DETAILED DESCRIPTION OF THE INVENTION

The present invention is directed to reactions that cause fouling during caustic washing of a propylene oxide product stream. As used herein, the term "fouling" is defined to refer to the reactions that ultimately result in the formation of a precipitate during caustic washing of a propylene oxide product stream. Without limiting the present invention to a particular mechanism of action, the inhibitors of the present invention are believed to inhibit fouling by inhibiting aldol condensation type reactions.

Certain amines have been found to inhibit fouling during caustic washing of a propylene oxide product stream. Suitable amines have the following general structure:

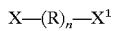

$$X-(R)_n-X^1$$

wherein X is selected from the group consisting of amino groups, and alkylamino groups wherein said alkyl comprises between about 1–5 carbon atoms; $X^1$ is selected from the group consisting of hydrogen, hydroxyl groups, amino groups, and alkylamino groups wherein said alkyl comprises between about 1–5 carbon atoms; n is between about 1–4; and, R is selected from the group consisting of ethyleneimino groups, arylene groups, and branched and unbranched alkylene groups having between about 2–10 carbon atoms, provided that, if R is a an ethyleneimino group, $X^1$ must be hydrogen.

In preferred inhibitors, R is either an alkylene group comprising between about 1–2 carbon atoms or an ethyleneimino group. Suitable inhibitors include, but are not necessarily limited to monoethanolamine, N,N'-di-sec-butyl-p-phenylenediamine, ethylenediamine, diethylene triamine, and triethylene tetramine. A preferred inhibitor is ethylenediamine. Such amine compositions are widely commercially available and/or can be manufactured by persons of ordinary skill in the art using well known procedures, such as those described in *Organic Chemistry*, R. T. Morrison and R. N. Boyd (5th ed. 1987) 939–941, incorporated herein by reference. As used herein, the term "amine" or "amine effective to inhibit" is defined to refer to an amine having the foregoing formula and amines that perform substantially the same function in substantially the same way to achieve substantially the same result.

The amines of the present invention preferably are injected into the propylene oxide product stream upstream of the caustic wash. The inhibitor feed rate may be based on the total pounds of "acetaldehyde" in the product stream (calculated on the assumption of 2.5 wt % of the propylene oxide product stream). For purposes of calculating the feed rate, the molar ratio of additive to "aldehyde" was calculated based on an assumption that all of the aldehydes present were acetaldehyde. Because other aldehydes may be present in the stream and may have molecular weights greater than acetaldehyde, the actual molar ratio may be slightly higher than the molar ratio calculated based upon this assumption. The inhibitor feed rate should be high enough to inhibit fouling, but as low as possible for the particular system in the interest of economic efficiency. Based on the current data, preferred feed rates are between a calculated molar ratio of about 3:1 to about 5:1. In the case of ethylenediamine, this corresponds to a weight basis of about 4.08/1 pounds of ethylenediamine/acetaldehyde to about 6.80/1 pounds of ethylenediamine/acetaldehyde. A ratio as low as 1:1 inhibitor/acetaldehyde should operate in the invention. In the case of ethylenediamine, this corresponds to a weight ratio of about 1.36/1 pounds of ethylenediamine/acetaldehyde.

The amine may be added; at the operating temperatures and pressures in the polypropylene oxide unit. Operating temperatures typically should range from ambient to about 87–88° C. (190° F.). Operating pressures typically range from atmospheric to about 40 psig. The amines of the present invention will react with the aldehyde carbonyls, or a condensation product of two or more reactive carbonyls, at ambient temperatures, and should operate to inhibit fouling at ambient temperatures as well.

The invention will be more readily understood with reference to the following examples.

EXAMPLE 1

A sample of a deposit from a fouled propylene oxide unit was obtained and analyzed for elemental composition and polymer make-up. The sample was analyzed for loss on ignition ("LOI") by placing the sample in a crucible, heating the sample to about 800° C. for about two hours, and measuring the weight difference of the sample before and after heating to determine percent organic weight content.

The LOI was 99.2 wt %, which indicated that the total organic content of the sample was approximately 99 wt %. The methylene chloride solubility of the sample was 50 wt %, which indicated that the methylene chloride soluble fraction had a lower molecular weight, or was composed of lower oligomers than the insoluble material. The "non-extractable" portion, or the portion of the sample that was not solubilized by methylene chloride, was analyzed by Fourier Transform Infrared (FT-IR), from which it was determined that the sample primarily contained the functional groups of aldehydes and possibly carboxylic acids. A comparison of the FT-IR scan of the deposit with a laboratory prepared aldol polymer showed some similarities.

The non-extractable portion was further analyzed using pyrolysis gas chromatography-mass spectrometry ("pyrolysis GC/MS"), the results of which primarily indicated the presence of acetaldehyde and propionaldehyde, with some carbon dioxide.

From the foregoing, it was concluded that acetaldehyde is the constituent of the aldehyde resin which forms as a result of aldol condensation polymerization in the caustic wash. The resin also may contain carboxylic acids and/or other functionalities.

EXAMPLE 2

The deposit of Example 1 was subjected to X-ray fluorescence analysis, which indicated that the sample also contained aluminum and sodium. Based on these results, and on the LOI of 99.2 wt %, it was determined that the inorganic materials are present in the sample only in extremely low concentrations, around 1 wt %. Of this 1 wt % inorganic material, 59 wt % was aluminum and 41 wt % was sodium.

EXAMPLE 3

A screening test was performed to ascertain agents that would reduce fouling during caustic washing of a propylene oxide product stream. Test inhibitors were added in the amounts shown in Table I to result in a molar ratio of inhibitor to acetaldehyde of: 5:1; 4:1; 3:1; 2:1; and, 1:1.

TABLE I

| Additive | MW | g for 5x | g for 4x | g for 3x | g for 2x | g for 1x |
|---|---|---|---|---|---|---|
| 38% sodium bisulfite | 120 | 8.4 | 6.72 | 5.04 | 3.36 | 1.68 |
| 55% MEA* | 61 | 2.9 | 2.32 | 1.74 | 1.16 | 0.58 |
| 37.5% EDA** | 60 | 4.2 | 3.36 | 2.52 | 1.68 | 0.84 |
| 85% DEHA*** | 89 | 2.8 | 2.24 | 1.68 | 1.12 | 0.56 |
| 12.5% bleach (NaOCl) | 74 | 16 | 12.8 | 9.6 | 6.4 | 3.2 |
| 25% UOP-5 in HAN**** | 219 | 23 | 18.4 | 13.8 | 9.2 | 4.6 |

*Monoethanolamine
**Ethylenediamine
***N,N-diethyl hydroxyl-amine, obtained from Atochem Chemical Co.
****UOP-5 is N,N'-di-sec-butyl-p-phenylenediamine obtained from Universal Oil Products, and "HAN" is heavy aromatic naphtha.

The foregoing inhibitors were used in the following experiment. A candidate was considered successful in these experiments if the deposit or precipitate did not form in the sample, or if the sample did not become viscous. A sample also was considered successful if a deposit or precipitate formed, but only after a longer period of time than in the blank.

EXAMPLE 4

100 ml disposable glass "medicine" bottles were placed in an ice bath in a fume hood. The bottles were dosed with the appropriate grams of inhibitor, then 78.1 g (94.1 wt %) of a propylene oxide product stream was added. Upon analysis for acetaldehyde content, the propylene oxide product stream was found to contain 2500 ppm of acetaldehyde. The bottles were capped and shaken 100 times, venting frequently to avoid pressure buildup in the bottle. The bottles then were dosed with 2.0 g of 21.1 vol % caustic (2 vol %) and 4.0 g (4 vol %) of deionized water. The bottles again were shaken vigorously and vented frequently. No inhibitor was added to one bottle, which was used as a control.

In a first experiment, the inhibitor was added at a 5:1 molar ratio of inhibitor to acetaldehyde based on an analysis which showed that the product stream contained 2500 ppm of aldehydes (assumed to be acetaldehyde for purposes of calculation). The samples dosed with ethylenediamine and monoethanolamine turned cloudy immediately after adding the polypropylene oxide to the inhibitors; however, both samples turned clear after the addition of the caustic and water mixture, demonstrating that MEA and DEA were effective inhibitors.

EXAMPLE 5

The same procedures were used to test 3:1 and 1:1 molar ratios of MEA and DEA. The results are shown in the following table:

| INHIBITOR DOSED | AFTER ABOUT 55 MINUTES |
|---|---|
| Blank | Yellow and cloudy |
| EDA 3:1 | Clear, colorless |
| EDA 1:1 | Cloudy, colorless |
| MEA 3:1 | Slightly yellow and clear |
| MEA 1:1 | Yellow and cloudy, almost like blank |

EXAMPLE 6

Some of the samples from Examples 4 and 5 were observed after approximately 24 hours and ranked as 1=best (yellow color) and 10=worst (orange with solids):

| INHIBITOR | AFTER 24 HOURS |
|---|---|
| Blank from Example 4 | Medium yellow - 5 |
| Blank from Example 5 | Thick material and dark yellow - 6 |
| ESA 1:1 from Example 5 | No solids, thick material - 6 |
| EDA 3:1 from Example 5 | No thickness, faint yellow |
| EDA 5:1 from Example 4 | No thickness - 3–4 |
| MEA 1:1 from Example 5 | Solids in bottom, very thick - 8–9 |
| MEA 3:1 from Example 5 | No solids, some thickness - 8 |
| MEA 5:1 from Example 4 | Very thick - 7 |

The sample containing the 5:1 molar ratio of EDA was analyzed by gas chromatography to determine whether the EDA was reacting with propylene oxide, which could reduce the product yield. The mixture contained 87% propylene oxide, 0.3–0.4% of the sample could not be identified (which is typical), and the remaining portion of the sample was the aqueous phase. From these results, it was concluded that no adverse reactions occurred between EDA and the propylene oxide.

Persons of ordinary skill in the art will appreciate that many modifications may be made to the embodiments described herein without departing from the spirit of the present invention. Accordingly, the embodiments described herein are illustrative only and are not intended to limit the scope of the present invention.

I claim:

1. A method for inhibiting fouling during caustic washing of a propylene oxide product stream comprising treating a mixture comprising a propylene oxide product stream and a caustic wash under conditions and with an amount of an amine effective to inhibit said fouling.

2. The method of claim 1 wherein said amine has the following general structure:

$$X-(R)_n-X^1$$

wherein

X is selected from the group consisting of amino groups, and alkylamino groups wherein said alkyl comprises between about 1–5 carbon atoms;

$X^1$ is selected from the group consisting of hydrogen, hydroxyl groups, amino groups, and alkylamino groups wherein said alkyl comprises between about 1–5 carbon atoms;

n is between about 1–4; and,

R is selected from the group consisting of ethyleneimino groups, arylene groups, and branched and unbranched alkylene groups having between about 2–10 carbon atoms, provided that, if R is a an ethyleneimino group, $X^1$ must be hydrogen.

3. The method of claim 2 wherein R is selected from the group consisting of an alkylene group comprising between about 1–2 carbon atoms and an ethyleneimino group.

4. The method of claim 1 wherein said amine is selected from the group consisting of monoethanolamine, N,N'-di-sec-butyl-p-phenylenediamine, ethylenediamine, diethylene triamine, and triethylene tetramine.

5. A method for inhibiting fouling during caustic washing of a propylene oxide product stream comprising treating a mixture comprising a propylene oxide product stream and a caustic wash under conditions effective to inhibit said fouling with an amount of an amine selected from the group consisting of ethylenediamine, diethylene triamine, and triethylene tetramine.

6. The method of claim 1 wherein:
said propylene oxide product stream comprises acetaldehyde; and
said amount comprises an amount sufficient to result in a calculated molar ratio of amine:acetaldehyde of between about 3:1 to about 1:20.

7. The method of claim 1 wherein
said propylene oxide product stream comprises acetaldehyde; and
said amount comprises an amount sufficient to result in a calculated molar ratio of amine:acetaldehyde of about 5:1.

8. The method of claim 2 wherein
said propylene oxide product stream comprises acetaldehyde; and
said amount comprises an amount sufficient to result in a calculated molar ratio of amine:acetaldehyde of between about 3:1 to about 1:20.

9. The method of claim 2 wherein
said propylene oxide product stream comprises acetaldehyde; and
said amount comprises an amount sufficient to result in a calculated molar ratio of amine: acetaldehyde of about 5:1.

10. The method of claim 4 wherein
said propylene oxide product stream comprises acetaldehyde; and
said amount comprises an amount sufficient to result in a calculated molar ratio of amine:acetaldehyde of between about 3:1 to about 1:20.

11. The method of claim 4 wherein
said propylene oxide product stream comprises acetaldehyde; and
said amount comprises an amount sufficient to result in a calculated molar ratio of amine:acetaldehyde of about 5:1.

12. The method of claim 5 wherein
said propylene oxide product stream comprises acetaldehyde; and
said amount comprises an amount sufficient to result in a calculated molar ratio of ethylenediamine:acetaldehyde of between about 3:1 to about 1:20.

13. The method of claim 5 wherein
said propylene oxide product stream comprises acetaldehyde; and
said amount comprises an amount sufficient to result in a calculated molar ratio of ethylenediamine:acetaldehyde of about 5:1.

14. The method of claim 1 wherein said conditions comprise a temperature of about 88° C. or less.

15. The method of claim 2 wherein said conditions comprise a temperature of about 88° C. or less.

16. The method of claim 5 wherein said conditions comprise a temperature of about 88° C. or less.

17. A method for inhibiting fouling during caustic washing of a propylene oxide product stream comprising treating a mixture comprising a propylene oxide product stream and a caustic wash at a temperature of about 88° C. or less under conditions and with an amount of an amide effective to inhibit said fouling, wherein said amide is selected from the group consisting of ethylenediamine, diethylene triamine, and triethylene tetramine.

18. A mixture comprising a propylene oxide product stream, a caustic wash solution, and an amount of an amine effective to inhibit fouling in said product stream.

19. The mixture of claim 18 wherein said amine has the following general structure:

$$X-(R)_n-X^1$$

wherein

X is selected from the group consisting of amino groups, and alkylamino groups wherein said alkyl comprises between about 1–5 carbon atoms;

$X^1$ is selected from the group consisting of hydrogen, hydroxyl groups, amino groups, and alkylamino groups wherein said alkyl comprises between about 1–5 carbon atoms;

n is between about 1–4; and

R is selected from the group consisting of ethyleneimino groups, arylene groups, and branched and unbranched alkylene groups having between about 2–10 carbon atoms, provided that, if R is a an ethyleneimino group, $X^1$ must be hydrogen.

20. The mixture of claim 17 wherein said amine is selected from the group consisting of ethylenediamine, diethylene triamine, and triethylene tetramine.

21. The mixture of claim 17 wherein
said propylene oxide product stream comprises acetaldehyde; and
said amount comprises an amount sufficient to result in a calculated molar ratio of amine:acetaldehyde of between about 3:1 to about 1:20.

22. The mixture of claim 17 wherein
said propylene oxide product stream comprises acetaldehyde; and
said amount comprises an amount sufficient to result in a molar ratio of amine:acetaldehyde of about 5:1.

23. The mixture of claim 18 wherein
said propylene oxide product stream comprises acetaldehyde; and
said amount comprises an amount sufficient to result in a calculated molar ratio of amine:acetaldehyde of between about 3:1 to about 1:20.

24. The mixture of claim 19 wherein
said propylene oxide product stream comprises acetaldehyde; and
said amount comprises an amount sufficient to result in a calculated molar ratio of ethylenediamine:acetaldehyde of between about 3:1 to about 1:20.

25. The mixture of claim 19 wherein
said propylene oxide product stream comprises acetaldehyde; and
said amount comprises an amount sufficient to result in a molar ratio of ethylenediamine:acetaldehyde of about 5:1.

* * * * *